United States Patent
Yamasaki et al.

(10) Patent No.: US 7,514,552 B2
(45) Date of Patent: Apr. 7, 2009

(54) CELLULOSE POWDER

(75) Inventors: Naoaki Yamasaki, Nobeoka (JP);
Kazuhiro Obae, Nobeoka (JP); Ichiro Ibuki, Nobeoka (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 11 days.

(21) Appl. No.: 10/557,052

(22) PCT Filed: May 28, 2004

(86) PCT No.: PCT/JP2004/007379

§ 371 (c)(1),
(2), (4) Date: Nov. 16, 2005

(87) PCT Pub. No.: WO2004/106416

PCT Pub. Date: Dec. 9, 2004

(65) Prior Publication Data

US 2007/0028801 A1 Feb. 8, 2007

(30) Foreign Application Priority Data

May 30, 2003 (JP) ............................ 2003-153814

(51) Int. Cl.
*C08B 1/00* (2006.01)

(52) U.S. Cl. .................. 536/56; 106/163.01; 106/203.2; 127/29; 127/37

(58) Field of Classification Search ............. 536/56; 106/163.01, 203.2; 127/29, 37
See application file for complete search history.

(56) References Cited

U.S. PATENT DOCUMENTS 3,146,168 A * 8/1964 Battista ............... 424/526

2004/0053887 A1 * 3/2004 Obae et al. ............ 514/57

FOREIGN PATENT DOCUMENTS

| CA | 2 427 991 | | 5/2003 |
|---|---|---|---|
| CA | 2 527 686 | | 12/2004 |
| EP | 1 036 799 | | 9/2000 |
| GB | 2 285 979 | | 8/1995 |
| GB | 2 285 979 | A | 8/1995 |
| JP | 40-26274 | | 7/1962 |
| JP | 40026274 | B * | 11/1965 |
| JP | 50-19917 | | 3/1975 |
| JP | 56-2047 | | 1/1981 |
| JP | 56-7713 | | 1/1981 |
| JP | 57-165392 | | 10/1982 |
| JP | 58-194808 | | 11/1983 |
| JP | 60-25919 | | 2/1985 |
| JP | 61-151116 | | 7/1986 |
| JP | 61-207341 | | 9/1986 |
| JP | 61-225121 | | 10/1986 |
| JP | 63-267731 | | 11/1988 |
| JP | 6-316535 | | 11/1994 |
| JP | 8-217801 | | 8/1996 |
| JP | 8-268914 | | 10/1996 |
| JP | 11-35487 | | 2/1999 |
| JP | 11-152233 | | 6/1999 |
| JP | 11152233 | * | 6/1999 |
| JP | 11/193229 | | 7/1999 |
| JP | 2000-16934 | | 1/2000 |
| JP | 2000-247869 | | 9/2000 |
| JP | 2001/181195 | | 7/2001 |
| JP | 2001-316248 | | 11/2001 |
| JP | 2001-335469 | | 12/2001 |
| JP | 2002-534455 | | 10/2002 |
| JP | 2003-161 | | 1/2003 |
| JP | 2003-55219 | | 2/2003 |
| WO | 02/02643 | | 1/2002 |

* cited by examiner

*Primary Examiner*—David M Brunsman
(74) *Attorney, Agent, or Firm*—Staas & Halsey LLP

(57) ABSTRACT

A cellulose powder which has an average degree of polymerization of 150 to 450, an average particle diameter of 30 to 250 μm, an apparent specific volume exceeding 7 cm$^3$/g, and a retention of polyethylene glycol having a molecular weight of 400 to 190% or higher.

6 Claims, No Drawings

CELLULOSE POWDER

This application is based on and hereby claims priority to International Application PCT/JP2004/007379, filed May 28, 2004 and Japanese Patent Application 2003-1 53814, filed May 30, 2003, the contents of which are hereby incorporated by reference.

TECHNICAL FIELD

The present invention relates to a cellulose powder, a method for preparing the cellulose powder, and a molded article composition containing the cellulose powder and one or more active ingredients. The composition is useful as an excipient for the molded article containing the active ingredient, which is used in the field of medicine, food, or other chemical industries, and particularly as an excipient for medicine tablets.

BACKGROUND ART

It has been previously and widely carried out to prepare molded articles containing active ingredients by using cellulose powder as an excipient.

Cellulose powders that were used are known to be microcrystalline celluloses and powdered celluloses, including the following examples.

JP-B-40-26274 describes a cellulose powder having an average polymerization degree of 150 to 375, an apparent specific volume of 1.84 to 8.92 $cm^3/g$, and a particle size of 300 μm or less.

JP-B-56-2047 describes a cellulose powder having an average polymerization degree of 60 to 375 and an apparent specific volume of 1.6 to 3.1 $cm^3/g$ and 2 to 80 wt % of a component of 200 meshes or more, and JP-A-06-316535 deals with cellulose powder having an average polymerization degree of 100 to 375, an apparent specific volume of 4.0 to 6.0 $cm^3/g$, and an average particle size of 30 to 120 μm without the substantial presence of a particle of 355 μm or more which is obtained by the acid hydrolysis or alkaline oxidative decomposition of a cellulosic material.

WO02/02643 describes a cellulose powder having an average polymerization degree of 150 to 450, an average particle size of 20 to 250 μm, and an apparent specific volume of 4.0 to 7.0 $cm^3/g$.

JP-A-11-152233 describes those cellulose powders having an average polymerization degree of 100 to 375 which pass through a sieve with a mesh size of 75 μm and of which 70% or more of the total weight remains on a sieve with a mesh size of 38 μm without passing therethrough.

JP-A-50-19917 describes a method for preparing an additive for tablet molding which includes pretreating purified pulp to depolymerize until the pulp has an average polymerization degree of 450 to 650, and then subjecting it to mechanical pulverization treatment such that 50% or more of the resulting particles may pass through a 200-mesh sieve.

JP-A-63-267731 describes a cellulose powder which is pulverized to an average particle size of 30 μm or less. JP-A-63-267731 describes a method of preparation of a cellulose powder having an average particle size of 10 μm or less. This reference describes a powder having a relatively large apparent specific volume.

However, there has been a problem that the cellulose powder obtained by the method disclosed in the above described reference has insufficient compression moldability because the compression moldability of it is low, and thus a tablet with practical hardness can not be obtained. Further, there has also been a problem that when an active ingredient has liquid or semisolid form, exudation of the ingredient and tableting disorder occur at the compression molding of the tablet.

In addition, when a liquid or semisolid active ingredient is formed into a tablet at ordinary temperature, a method that has been previously known, which includes holding the liquid ingredient directly on an adsorption carrier, or dissolving, emulsifying or suspending the active ingredient in water, organic solvent, water-soluble polymer or surfactant before the holding thereof on the adsorption carrier, and then passing a drying process, and further subjecting the resultant dry powder or granule to compression molding, is described in JP-A-56-7713, JP-A-60-25919, JP-A-61-207341, JP-A-11-193229, JP-A-11-35487, JP-A-2000-16934, JP-A-2000-247869, JP-A-2001-181195, JP-A-2001-316248, National Publication of International Patent Application No. 2002-534455, JP-A-2003-161, JP-A-2003-55219. In such a method it has been a problem that there are many necessary drying steps, and thus the costs of equipment which is used therein and the energy used for drying are increased.

Also, JP-A-61-151116 describes a method which involves mixing an active ingredient with a surfactant or a water-soluble polymer in the presence of a nonaqueous solvent, and then removing the solvent, and JP-A-61-225121 describes a method which involves dissolving the ingredient in liquid polyethylene glycol, and then obtaining a powder or a granule, followed by the compression molding. In such a method it has been a problem that the use of the nonaqueous solvent requires the step of desolvation under heating, and thus the costs of equipment which is used therein and energy used for drying are increased. When only polyethylene glycol is used without adding a solvent, no tablet has been substantially obtained. Indeed, only a powder is described in the Examples of these references.

JP-A-57-165392 discloses a method for preparing a tablet containing an active ingredient and 10% or more of fat and oil based on the weight of the active ingredient. However, in such a method the active ingredient, the fat and oil component and an excipient must be formed into a dry granule using a compression roller. The extra step and the extra equipment therefor increase costs.

JP-A-58-194808 describes a chewable tablet consisting of a mixture of a pretreated active ingredient composition composed of a fat and oil absorbing material, which is a typical crystalline cellulose having an edible fat and oil absorbed therein, and a binder, an antioxidant, a flavor and/or a colorant, a pretreated active ingredient composition composed of an active ingredient particle mixture, an edible oil, a binder, an emulsifier, a flavor, and a coloring agent, wherein the active ingredient particles are coated with other components such as the binder, and a pretreated auxiliary composition for direct compression tableting composed of a binder and a flavor. However, in the method described in the reference it has been a problem that in order to obtain the three kinds of compositions, the respective pretreatment steps are required and such additional steps make the preparation method complicated, and thus the cost of equipment which is used therein is expensive. In addition, such a method does not satisfy the purpose of obtaining a tablet having high hardness because it provides only a tablet with low hardness.

JP-A-8-268914 discloses a solid pharmaceutical composition containing an oil or an oily substance, an active ingredient, and a water-insoluble non-bridged polymer excipient which has an average particle size of more than 150 μm and is capable of binding water, and a method for preparing the same. However, in such a method it has been a problem that the oily substance, the active ingredient, water, and the specific water-insoluble non-bridged polymer need to be stirred with high shearing force and the equipment used for this method is necessary.

JP-A-2001-335469 describes a method for producing a solid preparation that is excellent in the elution of a water-insoluble bioactive ingredient and further has a proper hardness. The method includes mixing the bioactive ingredient, a nonionic surfactant and/or an anionic surfactant and allowing a water-swelling polymeric compound with a specific surface area of 5,000 cm$^2$/g or more to support the mixture, to which a general-purpose cellulose powder is then added, followed by the compression molding. In such a method, it has been a problem that the steps of mixing the drug with the surfactant(s) and allowing the specific water-swelling polymeric compound to support the mixture are necessary, and such additional steps make the production method complicated, and thus the cost of equipment which is used therein is expensive.

As described above, conventional methods have not been able to solve the problems that complex preparation processes lead to the increased cost of equipment and energy and that practical tablet hardness is not achieved at compression molding, generating exudation of liquid active ingredient and tableting disorder.

An object of the present invention is to provide a cellulose powder which is excellent in compression moldability and liquid retention when used as an excipient in the preparation of molded articles containing various active ingredients. Particularly in the preparation of a medical tablet, the present invention does not generate exudation of liquid active ingredient and tableting disorder and can produce a tablet having sufficient hardness in a simple and easy production process.

DISCLOSURE OF THE INVENTION

As the result of intensive studies for solving the above-described problems, the inventors discovered that physical properties of cellulose powder can be controlled within a specific range to provide a cellulose powder combining compression moldability and liquid ingredient retentiveness, thereby accomplishing the invention.

Thus, the present invention is as follows:

(1) A cellulose powder having an average polymerization degree of 150 to 450, an average particle size of 30 to 250 μm, an apparent specific volume of more than 7 cm$^3$/g, and a retention of polyethylene glycol with a molecular weight of 400 of 190% or more.

(2) A method for preparing the cellulose powder described in (1) above, which includes drying a cellulose dispersion liquid containing cellulose dispersion particles composed of a natural cellulosic material hydrolyzed to have an average polymerization degree of 150 to 450 and a medium wherein the cellulose dispersion particles have an average particle size of 50 μm or more.

(3) A molded article composition including one or more active ingredients and the cellulose powder described in (1) above.

The cellulose powder of the invention has advantages such as: the composition has desirable physical properties of compression moldability and liquid ingredient retentiveness; the composition can be produced by a simple method; and a molded article can be produced from the composition, which has proper hardness and does not exude a liquid active component or have tableting problems, particularly in the case of the compression molding of a liquid or semisolid active ingredient as well as a solid active ingredient.

BEST MODE FOR CARRYING OUT THE INVENTION

The present invention is specifically described below.

The cellulose powder of the invention should have an average polymerization degree of 150 to 450. An average polymerization degree of less than 150 is not preferred because of insufficient compression moldability. Also, an average polymerization degree of more than 450 tends to produce impaired moldability. This is because the hydrolysis of a raw material cellulose does not sufficiently proceed, and thus the amorphous portion of cellulose is aboundingly contained and fibrousness appears strongly to facilitate the elastic recovery. In addition, an average polymerization degree of more than 450 is not preferred because exudation of a liquid component and tableting disorder occur at compression molding even when the retention of polyethylene glycol described below is high.

The cellulose powder of the invention should have an average particle size of 30 to 250 μm. An average particle size of less than 30 μm is not preferred because when atomizing the particle, the surface thereof is excessively exposed to impact to reduce liquid component retentiveness. It is also not preferred because cellulose particles easily aggregate and, when mixing them with an active ingredient, the ingredient is not dispersed uniformly, thereby increasing the variation of the active ingredients of the resulting tablets. On the other hand, an average particle size of more than 250 μm is not preferred because an active ingredient is sometimes separated and segregated, during a pneumatic conveying, and this reduces content uniformity.

The cellulose powder of the invention should have an apparent specific volume of more than 7.0 cm$^3$/g. An apparent specific volume of 7.0 cm$^3$/g or less can not give sufficient dynamic strength to a lot of molded articles because of insufficient moldability. A larger apparent specific volume is preferred; the upper limit is not particularly restricted, but 13.0 cm$^3$/g is satisfactory. More than 13.0 cm$^3$/g is not preferred because the flowability of cellulose powders is deteriorated, cellulose particles become liable to aggregate and, when mixing them with an active ingredient, the ingredient is not dispersed uniformly, thereby increasing the variation of the active ingredient contents of the resulting tablets.

The cellulose powder of the invention should have a retention of polyethylene glycol with a molecular weight of 400 of 190% or more; the rate of 200% or more is preferred particularly the rate of 250% or more.

For a holding capacity of polyethylene glycol with a molecular weight of 400 of 190% or more, the cellulose powder of the invention can, when the molded article containing liquid and semisolid active ingredients is subjected to compression molding, hold the liquid active ingredient and prevent the exudation thereof. A retention of polyethylene glycol with a molecular weight of 400 of less than 190% is not preferred because, in compression molding along with a liquid active ingredient, the liquid ingredient is not fully held to produce the exudation of the ingredient into a powder layer and thus the contact between cellulose particles that serve as a binder becomes poor, sufficient dynamic strength to the molded article can not be given, thereby producing tableting disorder.

In order to set the holding capacity of polyethylene glycol with a molecular weight of 400 at 190% or more, at least the average polymerization degree and the apparent specific volume need to be controlled within a predetermined range.

A larger retention of polyethylene glycol is preferred; the upper limit is not particularly restricted, but 440% is satisfactory. As large as 440% will lead to the exhibition of full performance of the cellulose powder as an excipient.

A method for preparing the cellulose powder of the invention is described below.

The cellulose powder of the invention may be prepared, for example, by dispersing, in a suitable medium, a natural cellulosic material subjected to hydrolysis treatment, followed by drying the cellulose dispersion liquid. Here, a solid content containing the cellulosic material is subjected to hydrolysis treatment that may be isolated from the reaction solution obtained by the hydrolysis treatment, and separately dispersed in a suitable medium, followed by drying the prepared dispersion liquid, or, when the hydrolyzed solution, as it is, forms a cellulose dispersion liquid, this dispersion liquid may be directly dried.

Natural cellulosic materials may be of plant or animal origin, and include, for example, those fibrous materials derived from natural products containing celluloses such as a wood, bamboo, cotton, ramie, hoya, bagasse, kanaf, or bacterial cellulose, and the natural cellulosic materials preferably have cellulose I type crystalline structure. The raw material may use one kind of natural cellulosic material from the above described materials, or may use a mixture of two or more such cellulosic materials. These are preferably used in the form of purified pulps although a method for purifying pulps is not particularly restricted; any pulp including dissolving pulp, kraft pulp, or NBKP pulp may be used.

The hydrolysis method may be acid hydrolysis, alkaline oxidative decomposition, hydrothermal degradation, steam explosion, or the like, or a combination of two kinds of such methods.

In the above described preparation method, the suitable medium in which the solid content containing the cellulosic material subjected to hydrolysis treatment is dispersed is not particularly restricted if it is industrially used, and may use water and/or an organic solvent. Organic solvents include, for example, alcohols such as methanol, ethanol, isopropyl alcohol, butyl alcohol, 2-methylbutyl alcohol, and benzyl alcohol, hydrocarbons such as pentane, hexane, heptane, and cyclohexane, and ketones such as acetone, and ethyl methyl ketone. Preferred organic solvents include those used in pharmaceutical preparations, for example, and classified as solvents in "IYAKUHIN TENKAZAI JITEN 2000" (issued by Yakuji Nippo Limited). Water and organic solvents may be used alone or in a combination of two or more kinds; the dispersion may be once performed in one kind of medium, and removed from the medium, followed by dispersion in a different medium.

The average particle size of a cellulose dispersion particle present in the cellulose dispersion liquid should be 50 µm or more. When the average particle size is less than 50 µm, even if the cellulose dispersion liquid is dried, the specific volume decreases the compression moldability decreases and the liquid component retentiveness decreases. Particularly, although a dispersion liquid of cellulose with an average particle size of less than 50 µm contains a relatively large amount of cellulose dispersion particle component, even if the dispersion liquid aboundingly contained in the particle component is dried, a cellulose powder with excellent liquid component retentiveness can not be provided because the particle component has been exposed to excessive impact on the particle surface when atomized, and thus has a changed surface structure.

In order to obtain a cellulose dispersion particle with an average particle size of 50 µm or more in the above described cellulose dispersion liquid, for example, a cellulose dispersion liquid before the drying may be subjected to a controlled dehydration purification e.g. by decantation using a decanter so as to provide a water content of 40% or more.

In an alternative method, cellulose dispersion particles with an average particle size of 50 µm or more selected by sieving, or a dispersion liquid containing these particles may be separately dispersed in a suitable medium.

In addition, these methods may be used alone or in combination.

The drying method is not particularly restricted, but may be, for example, freeze-drying, spray drying, drum drying, tray drying, flash drying, vacuum drying, or drying with an organic solvent.

As used herein, "molded article composition" needs to contain one or more active ingredients and the cellulose powder of the invention, and their amounts are not particularly restricted. However, the typical ranges thereof are 0.001 to 99% in the active ingredient(s) and 1 to 99% in the cellulose powder. Further, the composition may be processed by a well-known method such as mixing, stirring, granulation, sizing, or tableting.

As used herein, "active ingredient" refers to a medicinal component for a medicine, an agrochemical component, a fertilizer component, a feed component, a food constituent, a cosmetic component, a dye, a perfume, a metal, a ceramic, a catalyst, or a surfactant, and may have any form including powdery, crystalline, oily, liquid, or semisolid form. The ingredient may be subjected to coating for the control of elution, the reduction of bitterness and so on. These active ingredients may be used alone or in a combination of two or more kinds.

Medicinal components for medicines include, for example, antipyretic analgesic anti-inflammatory, sedative hypnotic, drowsiness preventing, dizziness suppressing, children's analgesic, stomachic, antacid, digestive, cardiotonic, antiarrhythmic, hypotensive, vasodilator, diuretic, antiulcer, intestinal function-controlling, osteoporotic, antitussive expectorant, antiasthmatic, antimicrobial, pollakiuria-improving, and analeptic drugs, and vitamins, all of which are orally administered. These medicinal components may be used alone or in a combination of two or more kinds.

Oily or liquid active ingredients used in the invention may be medicinal components for medicines described in "Japanese Pharmacopeia", "Japanese Pharmaceutical Codex (Japanese standards of Pharmaceutical Ingredients)", "USP", "NF", or "EP", including, for example, teprenone, indomethacin-farnesyl, menatetrenone, phytonadione, vitamin A oil, fenipentol, vitamins such as vitamin D and vitamin E, higher unsaturated fatty acids such as DHA (docosahexaenoic acid), EPA (eicosapentaenoic acid), and liver oil, coenzyme Qs, and oil-soluble flavorings such as orange, lemon, and peppermint oils. As for the above described oily or liquid active ingredients such as vitamin E, there are various homologues and derivatives thereof that are used in the invention without particular restriction if they are in liquid form at ordinary temperature. These include, for example, dl-α-tocopherol, dl-α-tocopherol acetate, d-α-tocopherol, and d-α-tocopherol acetate; the gradient may freely use one kind, alone, selected from these components, or a combination of two or more such kinds.

Semisolid active ingredients include, for example, Chinese herbal medicines or crude drug extracts such as earthworm, licorice, cassia bark, peony root, moutan bark, Japanese valerian, zanthoxylum fruit, ginger, citrus unshiu peel, ephedra herb, nandina fruit, yellow bark, polygala root, platycodon root, plantago seed, plantago herb, shorttube lycoris, senega root, fritillaria bulb, fennel, phellodendron bark, coptis rhizome, zedoary, matricaria, gentian, oriental bezoar, animal bile, adenophorae radix, ginger, atractylodes lancea rhizome, clove, citrus unshiu peel, atractylodes rhizome, panax rhizome, ginseng, kakkonto, keihito, kousosan, saiko-keishito, shosaikoto, shoseiryuto, hangekobokuto, bakumondoto, hangekobokuto, and maoto, an oyster meat essence, propolis or an extract thereof, and coenzyme Qs; the gradient may use one kind, alone, selected from these components, or a combination of two or more such kinds.

In addition to the active ingredient and the cellulose powder, optionally, the tablet composition of the invention may freely contain other components such as a disintegrator, a binder, a fluidizing agent, a lubricant, a flavoring agent, a perfume, a coloring agent, or a sweetening agent.

Disintegrators may be those classified as disintegrator in "IYAKUHIN TENKAZAI JITEN 2000" (issued by Yakuji Nippo Limited) including celluloses such as croscarmellose sodium, carmellose, carmellose calcium, carmellose sodium, and hydroxypropyl cellulose of low degree of substitution, starches such as sodium carboxymethyl starch, hydroxypropyl starch, rice starch, wheat starch, corm starch, potato starch, and a partially pregelatinized starch, and synthetic polymers such as crospovidone and crospovidone copolymer; the disintegrator may freely use one kind, alone, selected from these components, or a combination of two or more such kinds.

Binders may be those classified as binder in "IYAKUHIN TENKAZAI JITEN 2000" (issued by Yakuji Nippo Limited) including saccharides such as sucrose, glucose, lactose, and fructose, sugar alcohols such as mannitol, xylitol, maltitol, erythritol, and sorbitol, water-soluble polysaccharides such as gelatin, pullulan, carrageenan, Locust bean gum, agar, glucomannan, xanthan gum, tamarind gum, pectin, sodium alginate, and gum arabic, celluloses such as crystalline cellulose, powdered cellulose, hydroxypropyl cellulose, and methylcellulose, starches such as a pregelatinized starch and starch glue, synthetic polymers such as polyvinylpyrrolidone, carboxy vinyl polymer, and polyvinyl alcohol, and inorganic compounds such as calcium hydrogenphosphate, calcium carbonate, hydrotalcite, and magnesium aluminosilicate; the binder may freely use one kind, alone, selected from these components, or a combination of two or more such kinds.

Fluidizing agents may be those classified as fluidizing agent in "IYAKUHIN TENKAZAI JITEN 2000" (issued by Yakuji Nippo Limited) including silicides such as hydrous silicon dioxide and light anhydrous silicic acid; the fluidizing agent may freely use one kind, alone, selected from these components, or a combination of two or more such kinds.

Lubricants may be those classified as lubricant in "IYAKUHIN TENKAZAI JITEN 2000" (issued by Yakuji Nippo Limited) including magnesium stearate, calcium stearate, stearic acid, sucrose fatty acid ester, and talc; the lubricant may freely use one kind, alone, selected from these components, or a combination of two or more such kinds.

Flavoring agents may be those classified as flavoring agent in "IYAKUHIN TENKAZAI JITEN 2000" (issued by Yakuji Nippo Limited) including glutamic acid, fumaric acid, succinic acid, citric acid, sodium citrate, tartaric acid, malic acid, ascorbic acid, sodium chloride, and 1-menthol; the flavoring agent may freely use one kind, alone, selected from these components, or a combination of two or more such kinds.

Perfumes may be those classified as aromatizing agent or perfume in "IYAKUHIN TENKAZAI JITEN 2000" (issued by Yakuji Nippo Limited) including oils such as orange, vanilla, strawberry, yoghurt, menthol, fennel oil, hemlock oil, and peppermint oil, and green tea powder; the perfume may freely use one kind, alone, selected from these components, or a combination of two or more such kinds.

Coloring agents may be those classified as coloring agent in "IYAKUHIN TENKAZAI JITEN 2000" (issued by Yakuji Nippo Limited) including certified colors such as Food Red No. 3, Food Yellow No. 5, and Food Blue No. 1, sodium copper chlorophyllin, titanium oxide, and riboflavin; the coloring agent may freely use one kind, alone, selected from these components, or a combination of two or more such kinds.

Sweetening agents may be those classified as sweetening agent in "IYAKUHIN TENKAZAI JITEN 2000" (issued by Yakuji Nippo Limited) including aspartame, saccharin, glycyrrhizic acid dipotassium salt, stevia, maltose, maltitol, starch syrup, and powdered sweet hydrangea leaf; the sweetening agent may freely use one kind, alone, selected from these components, or a combination of two or more such kinds.

Molded article compositions of the invention include, when used as medicines, solid preparations such as tablets, powders, subtle granules, granules, extracts, and pills. Without confining to medicines, the molded article compositions of the invention may be also used e.g. in foods such as confectionery, health foods, texture-improving agents, and dietary fiber-reinforcing agent, facial cakes, bath agents, animal drugs, diagnostic reagents, agricultural chemicals, fertilizers, and ceramic catalysts.

As used herein, "tablet" refers to a molded article obtained by compression molding that includes the cellulose powder of the invention, one or more active ingredients, and optionally other additives. A composition for a tablet, formulated with the cellulose powder of the invention has practical hardness obtained by a simple and easy method such as direct tableting without going through a complex process; however, any preparation method including a dry granule compression method, a wet granule compression method, wet granulation compression (extragranular addition of microcrystalline cellulose), or a method for preparing a multicore tablet using, as inner core, a tablet preliminarily subjected to compression molding may be also used.

Methods for preparing tablet compositions that include mainly one or more active ingredients and the cellulose powder of the invention are described below; however, these methods are only illustrative, and the advantages of the invention are not limited by these methods.

An active ingredient described below may have any form of solid, liquid, and semisolid ones, and may be used alone, or by the dissolution, suspension, or emulsification thereof in a medium.

Preparing methods include:

(i) a method which includes mixing the cellulose powder of the invention with an active ingredient, and carrying out compression molding;

(ii) a method which includes mixing an active ingredient preliminarily dissolved or dispersed in water with the cellulose powder of the invention, and carrying out compression molding;

(iii) a method which includes preliminarily dissolving an active ingredient in a small amount of organic solvent, dispersing it in water, mixing this solution with the cellulose powder of the invention, and carrying out compression molding;

(iv) a method which includes mixing an active ingredient preliminarily dissolved or dispersed in a water-soluble polymer or a water-soluble polymer aqueous solution with the cellulose powder of the invention, and carrying out compression molding;

(v) a method which includes mixing an active ingredient preliminarily dissolved or dispersed in a fat and oil with the cellulose powder of the invention, and carrying out compression molding. In addition, an active ingredient preliminarily dissolved in a large amount of organic solvent may be mixed with the cellulose powder of the invention, followed by compression molding using a well-known method. However, the use of this preparation method requires the drying of the resulting tablet to remove the organic solvent.

Of the above described preparation methods, the method described in (i) may be adapted to mix the cellulose powder of the invention with an active ingredient and carrying out compression molding. Other components including a "solubilizing agent" such as surfactant or oil and fat, a disintegrator, a binder, a fluidizing agent, a lubricant, a flavoring agent, a perfume, a coloring agent, or a sweetening agent may be optionally added when mixing the cellulose powder of the invention and the active ingredient. The other components may be used alone or in a combination of two or more kinds. The order of addition and mixing of these components is not restricted; the active ingredient may be added to and mixed with the cellulose powder of the invention, or vice versa, or both may be collectively added and mixed. When other components are added in addition to the cellulose powder of the invention and an active ingredient, the cellulose powder of the invention may be added to and mixed with such components which are preliminarily mixed with the active ingredient, the active ingredient may be added to and mixed with the components which are preliminarily mixed with the cellulose powder, such components may be added to and mixed with the cellulose powder of the invention which is preliminarily mixed with the active ingredient, or all of each component may be collectively added and mixed. A method for adding the active component is not particularly restricted if it is carried out by the usual method; the addition may be continuously performed using a small-size sucking transporter, an air transporter, a bucket conveyor, a force-feed type conveying device, a vacuum conveyor, an oscillating type constant quantity feeder, a splay, a funnel, or the like, or may be collectively carried out. A mixing method is not particularly restricted if it is carried out by the usual method; it may use a vessel rotation type mixer such as a V type, W type, double corn type, or container tack type mixer, a stirring mixer such as a high-speed agitation type, universal agitation type, ribbon type, pug type, or nautor type mixer, a super mixer, a drum type mixer, or a fluidized bed type mixer. In addition, a vessel shaking type mixer such as a shaker may be also used. A method for the compression molding of the composition is not particularly restricted if it is carried out by the usual method; a method which includes using a mortar and a pestle for making the composition into a desired form by means of the compression molding or a method which includes preliminarily making the composition into sheet form by means of the compression molding, and cutting into a desired form may be used. A compression molding machine may use, for example, a roller type press such as a hydrostatic press, a briquetting roller type press, or a smoothing roller type press, or a compressor such as a single-punch tableting machine or a rotary tableting machine.

Of the above described preparation methods, such as the method described in (ii), which includes mixing an active ingredient preliminarily dissolved or dispersed in water with the cellulose powder of the invention and carrying out compression molding, a "solubilizing agent" such as surfactant or fat and oil, and the like may be optionally added in dissolving or dispersing the active ingredient in water as pretreatment. These may be used alone or in a combination of two or more kinds. The order of the addition and mixing of these components in dissolution or dispersion is not particularly restricted; the active ingredient may be added to and mixed with water, or vice versa, or both may be collectively added and mixed. When a solubilizing agent is added, a mixture of the active ingredient and the solubilizing agent may be added to and mixed with water, the active ingredient may be added to and mixed with the solubilizing agent dissolved or dispersed in water, or all of the components may be collectively added and mixed. A dissolution or dispersion method is not particularly restricted if it is carried out by the usual dissolution or dispersion method; a stirring/mixing method such as a portable mixer, a spatial mixer, a side mixer, or the like using the stirring blade of the one-way rotating, multi-shaft rotary, reciprocating/reversing, vertically moving, rotating+vertically moving, or duct type, a jet-type stirring/mixing method such as a line mixer, a gas-blowing stir ring/mixing method, a mixing method using a high-shear homogenizer, a high-pressure homogenizer, an ultrasonic homogenizer, or the like, or a mixing method of vessel shaking type using a shaker, or the like may be used. When the resulting solution or dispersion liquid is obtained from the above described method and mixed with the cellulose powder of the invention, other components such as a disintegrator, a binder, a fluidizing agent, a lubricant, a flavoring agent, a perfume, a coloring agent, a sweetening agent, or a solubilizing agent may be added. These may be used alone or in a combination of two or more kinds. The order of the addition and mixing of these components is not restricted; the active ingredient solution or dispersion liquid may be added to and mixed with the cellulose powder of the invention, or vice versa. When other components are added in addition to the cellulose powder of the invention and the active ingredient solution or dispersion liquid, the active ingredient solution or dispersion liquid may be added to and mixed with such components which are preliminarily mixed with the cellulose powder, the cellulose powder may be added to and mixed with such components which are preliminarily mixed with the active ingredient solution or dispersion liquid, such components may be added to and mixed with the cellulose powder of the invention which is preliminarily mixed with the active ingredient solution or dispersion liquid, or all of each component may be collectively added and mixed. In these cases, the adding, mixing, and compression molding methods are not particularly restricted if they are carried out by the usual methods; the methods illustrated in the preparing method of (i) may be also used.

In the case of the method which includes preliminarily dissolving an active ingredient in a small amount of organic solvent and then dispersing it in water, mixing this solution with the cellulose powder of the invention and carrying out compression molding, as described in (iii), the dissolution of the active ingredient in a small amount of organic solvent as pretreatment does not particularly restrict the order of addition; the active ingredient may be added to and mixed with the organic solvent, or vice versa, or both may be collectively added and mixed. In dispersing the active ingredient solution in water, one or more solubilzing agents may be used in combination therewith. In these cases, the order of addition is not particularly restricted; a mixture of the active ingredient solution and the solubilizing agent may be added to and mixed with water, the active ingredient solution may be added to and mixed with the solubilizing agent dissolved or dispersed in water, the solubilizing agent may be added to and mixed with a mixture of water and the active ingredient solution, or all of each component may be collectively added and mixed. The dissolving and dispersing methods are not particularly restricted if they are carried out by the usual dissolving and dispersing methods; the dissolving and dispersing methods illustrated in the preparation method of (ii) may be used. When the resulting active ingredient solution or dispersion liquid obtained by the above described method is mixed with the cellulose powder of the invention, a disintegrator, a binder, a fluidizing agent, a lubricant, a flavoring agent, a perfume, a coloring agent, a sweetening agent, a solubilizing agent, or the like may be optionally added. These may be used alone or in a combination of two or more kinds. In these cases, the adding, mixing, and compression molding methods are not particularly restricted; the methods illustrated in the preparation method of (i) may be used.

In the case of the method, described in (iv), which includes mixing an active ingredient preliminarily dissolved or dispersed in a water-soluble polymer or a water-soluble polymer aqueous solution with the cellulose powder of the invention and carrying out compression molding, a solubilizing agent may be optionally added in dissolving or dispersing the active ingredient in the water-soluble polymer or the water-soluble polymer aqueous solution as pretreatment. The order of addition of these components is not particularly restricted; for example, the active ingredient may be added to and mixed with the water-soluble polymer or the water-soluble polymer aqueous solution, or vice versa, or both may be collectively added and mixed. When a solubilizing agent is added, the order of addition also is not particularly restricted; a mixture of the active ingredient and the solubilizing agent may be added to and mixed with the water-soluble polymer or the water-soluble polymer aqueous solution, a mixture of the water-soluble polymer or the water-soluble polymer aqueous solution and the solubilizing agent may be added to and mixed with the active ingredient, a mixture of the active ingredient and the water-soluble polymer or the water-soluble polymer aqueous solution may be added to and mixed with the solubilizing agent, or each component may be collectively added and mixed. When the resulting active ingredient solution or dispersion liquid obtained by the above described method is mixed with the cellulose powder of the invention, a disintegrator, a binder, a fluidizing agent, a lubricant, a flavoring agent, a perfume, a coloring agent, a sweetening agent, a solubilizing agent, or the like may be added. These may be used alone or in a combination of two or more kinds. In these cases, the adding, mixing, and compression molding methods are not particularly restricted; the methods illustrated in the preparation method of (i) may be used.

In the case of the method, described in (v), which includes mixing an active ingredient preliminarily dissolved or dispersed in a fat and oil with the cellulose powder of the invention and carrying out compression molding, a solubilizing agent may be optionally added in dissolving or dispersing the active ingredient in the fat and oil as pretreatment. Methods for adding, dissolving, and dispersing these components are not particularly restricted; the methods illustrated in the preparation method of (iv) may be used. When the resulting active ingredient solution or dispersion liquid is mixed with the cellulose powder of the invention, a disintegrator, a binder, a fluidizing agent, a lubricant, a flavoring agent, a perfume, a coloring agent, a sweetening agent, a solubilizing agent, or the like may be optionally added. These may be used alone or in a combination of two or more kinds. In these cases, the adding, mixing, and compression molding methods are not particularly restricted; the method illustrated in the preparation method of (i) may be used.

In these preparation methods, particularly when the active ingredient is poorly soluble in water, the resulting composition can have the solubility or the dispersibility of the active ingredient in water improved by using methods (i) to (v) involving the addition of a solubilizing agent or methods (iii), (iv), and (v) that do not involve the addition of the solubilizing agent.

Organic solvents used in the above described preparing method are not particularly restricted if they are used in medicines, and may be, for example, those classified as solvent in "IYAKUHIN TENKAZAI JITEN 2000" (issued by Yakuji Nippo Limited) including alcohols such as methanol and ethanol and ketones such as acetone; these may be used alone or in a combination of two or more kinds.

Water-soluble polymers may be, for example, water-soluble polymers described in "IYAKUHIN TENKAZAI JITEN 2000" (issued by Yakuji Nippo Limited) including hydroxypropyl cellulose, hydroxypropyl methylcellulose, polyacrylic acid, carboxy vinyl polymer, polyethylene glycol, polyvinyl alcohol, polyvinylpyrrolidone, methylcellulose, ethylcellulose, gum arabic, starch glue, or the like; these may be used alone or in a combination of two or more kinds.

Fat and oils may be, for example, fat and oils described in "IYAKUHIN TENKAZAI JITEN 2000" (issued by Yakuji Nippo Limited) including monoglyceride stearate, triglyceride stearate, sucrose stearate, paraffins such as liquid paraffin, carnauba wax, hydrogenated oils such as hydrogenated castor oil, castor oil, stearic acid, stearyl alcohol, polyethyleneglycol, or the like; these may be used alone or in a combination of two or more kinds.

Surfactants may be, for example, those classified as a surfactant in "IYAKUHIN TENKAZAI JITEN 2000" (issued by Yakuji Nippo Limited) including phospholipid, glycerin fatty acid ester, polyethylene glycol fatty acid ester, sorbitan fatty acid ester, polyoxyethylene hardened castor oil, polyoxyethylene cetyl ether, polyoxyethylene stearyl ether, polyoxyethylene nonylphenyl ether, polyoxyethylene polyoxypropylene glycol, polyoxyethylene sorbitan monolaurate, polysorbate, sorbitan monooleate, glyceride monostearate, monooxyethylene sorbitan monopalmitate, monooxyethylene sorbitan monostearate, polyoxyethylene sorbitan monooleate, sorbitan monopalmitate, and sodium lauryl sulfate; these may be used alone or in a combination of two or more kinds.

In addition to using the form of a tablet obtained by compression molding as described above, the composition for a tablet according to the invention may be used in the form of a granule or a powder particularly for the purpose of improving flowability, blocking resistance, and aggregation resistance because the composition is excellent in liquid component retentiveness.

In addition, the cellulose powder of the invention has extremely high moldability compared to conventional cellulose powders, thus may allow when blended in a large quantity in a tablet, the tablet to maintains the shape thereof without disintegrating in a solvent, enabling the release of an active ingredient to be controlled. Therefore, it is also useful as a matrix-type controlled release base.

Further, when a low-melting drug, a fat and oil, a liquid, and a semisolid drug, supported by an excipient or the like are subjected to tableting using a well-known method, the blending of the cellulose powder of the invention has effect of noticeably preventing the following disadvantages including sticking generated by reduced tableting pressure, and capping or lamination generated by increased tableting pressure. Particularly, the cellulose powder of the invention may avoid the above disadvantages of tableting at a smaller amount than conventionally known crystalline celluloses or powdered celluloses, and thus has the advantageous effects of enabling the drug content to be increased or to decrease the size of the tablet. When used in an amount enough to inhibit such the disadvantages of tableting, it has the following advantages which have not been found in conventional excipients, in addition to providing the tablet to high hardness and friability, in terms of having ease of handling such as the reduction of scattering and enabling the content uniformity to be ensured because the present invention does not produce separation or segregation during pneumatic conveying compared to an inorganic additive used previously as a sticking inhibitor (for example, calcium silicate, light anhydrous silicic acid, magnesium aluminometasilicate, or the like).

EXAMPLES

The present invention is described based on the following Examples. However, the embodiments of the invention are not intended to be limited to descriptions of these Examples.

Methods for measuring various physical properties in Examples and Comparative Examples are as follows.

(1) Average Polymerization Degree

The degree used a value determined by the copper ethylenediamine solution viscosity method described in the Identification Test for Crystalline Cellulose (3) of The Japanese Parmacopoeia, Fourteenth Edition.

(2) The Average Particle Size (μm) of a Cellulose Particle in Dispersion Liquid

The particle sizes were determined, by a predetermined method, using, as samples, cellulose dispersions-obtained during the cellulose powder production described in Examples and Comparative Examples, employing a laser diffraction/scattering particle size distribution meter (LA-910 from Horiba, Ltd.). The average particle size was calculated in the form of the number average of volume frequencies.

(3) The Average Particle Size (μm) of a Cellulose Powder

The average particle size of a powder sample was determined by sifting 10 g of the sample for 10 minutes using a Ro-Tap type sieve shaker (Sieve Shaker A Type from Taira Kosakusho Ltd.) to measure the particle size distribution, representing as a cumulative weight 50% particle size. The average particle size of such dried cellulose powders, and the average particle size of cellulose dispersion particles in the dispersion liquid by the laser diffraction/scattering method in (2) are measured using totally different principles, and thus values obtained in the respective measurements do not correlate well with each other.

(4) Apparent Specific Volume ($cm^3/g$)

The apparent specific volume is a value obtained by roughly filling a 100 $cm^3$ glass measuring cylinder with a powder sample over 2 to 3 minutes using a metering feeder or the like, horizontally leveling the top face of the powder layer using a soft brush like a hair pencil, reading the volume, and dividing the read value by the weight of the powder sample. The Powder by weight was set as appropriate so that the volume is on the order of 70 to 100 $cm^3$.

(5) The Retention (% by Weight) of Polyethylene Glycol with an Average Molecular Weight of 400

A cellulose sample (2.0 g) was kneaded on a glass board using a spatula each time while adding dropwise polyethylene glycol (Polyethylene Glycol 400 from Sanyo Chemical Industries, Ltd.) from a burette to use, as an end point, the point at which macrogol bleeds out on the powder surface to calculate a saturated retention percentage (%) employing the following calculating formula:

Saturated retention=(the weight of macrogol absorbed by a cellulose powder)×100/(the weight of the cellulose powder)

(6) Tablet Hardness (N)

A columnar molded article or a sample tablet prepared from a powder sample by a predetermined method was loaded along the diameter of the molded article or the tablet using Shleuniger hardness tester (Model 6D from Freund Industrial Co., Ltd.) to determine the load at breakage. It was represented as the number average of measurements with three samples.

(7) Exudation of a Liquid Component

The exudation of a liquid component on the tablet surface obtained by compression molding was visually observed.

(8) The Occurrence Rate (%) of Tableting Disorder

The occurrence rate percentage (%) of the tableting disorder was obtained by visually inspecting the tableting for sticking, chipping, capping, or lamination. The number of tablets with tableting disorder are divided by the total number of tablets to calculate the percentage.

Example 1

Two (2) kg of a chopped commercial pulp (polymerization degree: 1030) and 30 L of a 4 N hydrochloric acid aqueous solution for hydrolysis were placed in a low-speed stirrer (30LGL Reactor, blade diameter: about 30 cm, from Ikebukuro Horo Kogyo Co., Ltd.) at 40° C. for 24 hours for stirring at a stirring rate of 5 rpm to provide an acid-insoluble residue having an average polymerization degree of 310. The resulting acid-insoluble residue was filtered to provide a solid content of 40% using a nutsche, which was further washed with purified water, neutralized with aqueous ammonia, and then placed in a 90-L plastic bucket, to which purified water was then added, followed by stirring at a stirring rate of 5 rpm using Three One Motor (Type 1200G, 8M/M, stirring blade diameter: 5 cm, from Heidon) to make a cellulose dispersion liquid with a solid content concentration of 10% (the average particle size of a cellulose particle in the cellulose dispersion liquid was 67 μm. This was subjected to spray drying (dispersion liquid feed rate: 6L/hr, inlet temperature: 180 to 220° C., outlet temperature: 50 to 70° C.) to provide cellulose powder A. The physical properties of cellulose powder A are shown in Table 1.

Example 2

A commercial pulp (polymerization degree: 790) was used to carry out the same operation in Example 1 except for setting hydrolysis time to 48 hours to provide an acid-insoluble residue with an average polymerization degree of 270. The resulting acid-insoluble residue was filtered, neutralized, and stirred using the same operation as that in Example 1 to provide a cellulose dispersion liquid with a solid content concentration of 22% (the average particle size of a cellulose particle in the cellulose dispersion liquid was 54 μm.). The resulting cellulose dispersion liquid was also subjected to spray drying using the same operation in Example 1 to provide cellulose powder B. The physical properties of cellulose powder B are shown in Table 1.

Example 3

A commercial pulp (polymerization degree: 840) was used to carry out the same operation in Example 1 except for setting hydrolysis conditions to a 5 N hydrochloric acid aqueous solution, 40° C., and 60 hours to provide an acid-insoluble residue with an average polymerization degree of 160. The resulting acid-insoluble residue was washed using purified water without filtering, and neutralized; And then by means of a sieve with an opening of 38 μm without stirring, the passing material was then removed to provide a cellulose dispersion liquid with a solid content concentration of 10% (the average particle size of a cellulose particle in the cellulose dispersion liquid was 59 μm.). The resulting cellulose dispersion liquid was subjected to spray drying using the same operation in Example 1 to provide cellulose powder C. The physical properties of cellulose powder C are shown in Table 1.

Example 4

A commercial pulp (polymerization degree: 790) was used to carry out the same operation in Example 1 except for setting hydrolysis conditions to a 5 N hydrochloric acid aqueous solution, 40° C., 4 hours, and a stirring rate of 30 rpm to provide an acid-insoluble residue with an average polymerization degree of 440. The resulting acid-insoluble residue was filtered and neutralized using the same operation as that in Example 1, and then stirred at a stirring rate of 500 rpm to provide a cellulose dispersion liquid with a solid content concentration of 17% (the average particle size of a cellulose particle in the cellulose dispersion liquid was 51 μm.). The resulting cellulose dispersion liquid was dried using a drum dryer (from Kusunoki Co., Ltd., Model KDD-1, steam pressure: 0.35 MPa, drum surface temperature: 136° C., drum rotation number: 2 rpm, temperature of the aqueous dispersion in a liquid-storing portion of the drum dryer: 100° C.), pulverized by a hammer mill, and by means of a sieve with an opening of 425 μm, coarse particles were then removed to provide cellulose powder D. The physical properties of cellulose powder D are shown in Table 1.

Example 5

A pulverized commercial pulp (polymerization degree: 1030) was immersed in a sodium hypochlorite solution with an available chlorine of 1.6 g/L to set pH to 10.9, and this was treated at 60° C. for 6 hours. The treated pulp was well washed with water, subjected to centrifugal dehydration and then to blast drying at 105° C., and pulverized for 10 minutes using a household mixer. The resulting pulverized pulp (2 kg) was hydrolyzed, under conditions of 4 N hydrochloric acid aqueous solution, 40° C., and 15 hours, using the same method as that in Example 1 to provide an acid-insoluble residue having an average polymerization degree of 300. The resulting acid-insoluble residue was filtered, neutralized, and stirred using the same operation in Example 1 to provide a cellulose dispersion liquid with a solid content concentration of 10% (the average particle size of a cellulose particle in the cellulose dispersion liquid was 65 μm.). The resulting cellulose dispersion liquid was subjected to the spray drying using the same operation in Example 1 to provide cellulose powder E. The physical properties of cellulose powder E are shown in Table 1.

Comparative Example 1

The hydrolysis was carried out using the same operation in Example 1 except for setting hydrolysis conditions to 3 N hydrochloric acid aqueous solution, 40° C., and 20 hours and a stirring rate of 20 rpm during reaction to provide an acid-insoluble residue having an average polymerization degree of 440. The resulting acid-insoluble residue was filtered to provide a solid content of 70% using a nutsche. The resulting filtration residue was further washed with purified water, neutralized with aqueous ammonia, and then placed in a 90-L plastic bucket, to which purified water was then added, followed by stirring at a stirring rate of 100 rpm using the same operation as that in Example 1 to make a cellulose dispersion liquid with a solid content concentration of 6% (the average particle size of a cellulose particle in the cellulose dispersion liquid was 41 μm.). The resulting cellulose dispersion liquid was subjected to the spray drying using the same operation in Example 1 to provide cellulose powder F (corresponding to Example 7 in WO02/02643 above). The physical properties of cellulose powder F are shown in Table 1.

Comparative Example 2

The hydrolysis was carried out using the same operation in Example 1 except for setting hydrolysis conditions to 0.14 N hydrochloric acid aqueous solution, 121° C., and 1 hour and a stirring rate during reaction of 30 rpm to provide an acid-insoluble residue having an average polymerization degree of 220. The resulting acid-insoluble residue was filtered to provide a solid content of 70% using a nutsche. The resulting filtration residue was further washed with purified water, neutralized with aqueous ammonia, and then placed in a 90-L plastic bucket, to which purified water was then added, followed by stirring at a stirring rate of 500 rpm using the same operation in Example 1 to make a cellulose dispersion liquid with a solid content concentration of 17% (the average particle size of a cellulose particle in the cellulose dispersion liquid was 29 μm.). The resulting cellulose dispersion liquid was subjected to the spray drying as described in Example 1, from which, using a sieve with an opening of 325 mesh, coarse particles were then removed to provide cellulose powder G (corresponding to Example 1 in JP-B-40-26274 above). The physical properties of cellulose powder G are shown in Table 1.

Comparative Example 3

A pulp sheet in which acicular and broad leaf trees were mixed and dissolved (α-cellulose: 90.5%, β-cellulose: 4.7%, cuprammonium relative viscosity: 4.70, whiteness degree: 93) was ground and immersed in a sodium hypochlorite solution with an available chlorine content of 1.6 g/L to set pH to 10.9, and this was treated at 60° C. for 310 minutes (the average particle size of a cellulose particle in the cellulose dispersion liquid was 50 μm.). The treated pulp was well washed with water, and subjected to centrifugal dehydration and then to blast drying at 105° C. This pulp was pulverized for 15 minutes using a household mixer (Model SM-L56, from Sanyo Electric Co., Ltd.), and then, by a sieve with an opening of 80 mesh, coarse particles were then removed to provide cellulose powder H (corresponding to Example 2 in JP-A-50-19917 above). The physical properties of cellulose powder H are shown in Table 1.

Comparative Example 4

A commercial pulp (polymerization degree: 1030) (500 g) was pulverized for 30 minutes in a household mixer (Model SM-L56, from Sanyo Electric Co., Ltd.), and then, by a sieve with an opening of 150 μm, coarse particles were then removed to provide cellulose powder I (the average particle size of a cellulose particle in a cellulose dispersion liquid can not be described because of bypassing a cellulose dispersion). The physical properties of cellulose powder I are shown in Table 1.

Comparative Example 5

Cellulose powder G obtained in Comparative Example 2 was pulverized using a pneumatic pulverizer (Single Track Jet Mill Model STJ-200 from Seishin Enterprise Co., Ltd.) to provide cellulose powder J (corresponding to Example 1 in JP-A-63-267731 above). The physical properties of cellulose powder J are shown in Table 1.

Comparative Example 6

Cellulose powder F obtained in Comparative Example 1 was subjected to the removal of coarse particles using a sieve with an opening of 75 μm on an air jet sieve (from Alpine Co.), and fine particles were then removed using a sieve with an opening of 38 μm (a method described in Examples of JP-A-11-152233 above) to provide cellulose powder K. The physical properties of cellulose powder K are shown in Table 1.

Comparative Example 7

The hydrolysis was carried out using the same operation as that in Example 1 except for setting hydrolysis conditions to 0.14 N hydrochloric acid aqueous solution, 121° C., and 1 hour and a stirring rate of 30 rpm during reaction to provide an acid-insoluble residue having an average polymerization degree of 220. The resulting acid-insoluble residue was filtered to provide a solid content of 70% using a nutsche. The filtration residue was further washed with purified water, neutralized with aqueous ammonia, and then placed in a 90-L plastic bucket, to which purified water was then added, followed by stirring at a stirring rate of 500 rpm using the same operation in Example 1 to make a cellulose dispersion liquid with a solid content concentration of 4% (the average particle size of a cellulose particle in the cellulose dispersion liquid was 29 μm.). The resulting cellulose dispersion liquid was subjected to spray drying using the same operation as that in Example 1, from which, using a sieve with an opening of 400 mesh, coarse particles were then removed to provide cellulose powder L (corresponding to a bulk density of 8.92 cm$^3$/g in JP-B-40-26274 above). The physical properties of cellulose powder L are shown in Table 1.

Examples 6 to 10

To 10 g of a commercial crystalline cellulose (Avicel PH-101 from Asahi Chemical Industry Co., Ltd.) was added 6.5 g of macrogol 400 (from Sanyo Chemical Industries, Ltd.) as one example of a liquid active ingredient, followed by stirring and mixing for 10 minutes using a spatula in a glass beaker, to which 2.5 g of light anhydrous silicic acid (Aerosil 200 from Nippon Aerosil Co., Ltd.) was further added, followed by stirring and mixing for 5 minutes using a spatula. 3.5 g of the resulting mixed powder was mixed with each 1.5 g of celluloses A to E obtained in Examples 1 to 5 in polyethylene bags for 3 minutes (the final compositional weight ratio in each mixed powder is cellulose powder/PH-101/Aerosil/macrogol=30/37.8/9.5/22.7).

In a mortar (using the material SUK2, 3, from Kikusui Seisakusho Ltd.) was placed 0.2 g of each of the resulting mixed powder samples which was then compressed at a compression stress of 100 MPa employing a circular plane pestle (using the material SUK2, 3, from Kikusui Seisakusho Ltd.). The compression was kept for 10 seconds to produce a columnar molded article (PCM-1A from Aikoh Engineering Co., Ltd. was used as a compressor). The hardness of the resulting each columnar molded article is shown in Table 2. Here, as the result of observing tablet surface appearance and adhesion to the pestle with eyes, no tablet showed exudation of a liquid component and also adhesion of the tablet composition to the pestle.

Comparative Examples 8 to 14

Cellulose powders F to L obtained in Comparative Examples 1 to 7 were used as cellulose powders to provide columnar molded articles using a similar operation to that in Examples 6 to 10. The hardness of resulting each columnar molded article is shown in Table 2. As the result the tablet surface appearance and adhesion to the pestle was observed to be in a similar way to Examples 6 to 10, all tablets showed exudation of a liquid component and adhesion of the tablet composition to the pestle, and the tableting disorder of sticking had been generated.

In addition, cellulose powders H and I, which have an average polymerization degree of more than 450, are considered to have produced exudation of the liquid component on the tablet surface and tableting disorder during compression probably because, while they have a high retention of polyethylene glycol, the liquid component is retained not in an intraparticular space but in an interparticular one.

Any of the tablets using cellulose powders A to E obtained by the operations in Examples 1 to 5 showed a hardness of 40 N or more, and did have a practical tablet hardness (40 N or more) at which tablets are generally considered not to be abraded when they are conveyed in a process or transported in a state stored within a bottle. In contrast, the tablets using cellulose powders F to K obtained by the operations in Comparative Examples 1 to 6 only showed a hardness of less than 40 N, and did not have a practical tablet hardness.

Example 11

500 g of a commercial crystalline cellulose (Avicel PH-301 from Asahi Chemical Industry Co., Ltd.) was added to 150 g of commercial dl-α-tocopherol (from Wako Pure Chemical Industries Ltd.) dissolved in macrogol 400 at a weight ratio of 1:1, with stirring at a stirring rate of 63 rpm using a planetary mixer (the universal mixing stirrer 50M-03-R from Sanei Seisakusho Co., Ltd.), which was then mixed for 10 minutes, followed by further adding 65.3 g of Aerosil 200 before mixing for 5 minutes. With 350 g of the resulting mixed powder was mixed cellulose powder A in a polyethylene bag for 3 minutes, to which magnesium stearate (from Taihei Chemical Industrial Co., Ltd.) was then added in an amount of 0.5 wt % based on the total weight of the mixed powder, followed by further mixing for 0.5 minute to provide a mixed powder for tableting (The final compositional weight ratio in the mixed powder is cellulose powder/PH-i 01 /Aerosil/the macrogol solution of drug/magnesium stearate =30/49/6.3/14.7/0.5). That is, the weight ratio of pre-magnesium stearate ingredients/magnesium stearate is 100/0.5.

The mixed powder was subjected to tableting at a turn table rotation rate of 22 rpm and compressive forces of 5,000 N, 10,000N, and 15,000 N using a circular plane pestle 0.8 cm in diameter in a rotary tableting machine (Cleanpress Correct 12HUK, Stirring Feeder, from Kikusui Seisakusho Ltd.) to make tablets each having a weight of 170 mg. The physical properties of the tablets are shown in Table 3. As the result of visual observation of the tablet surface appearance and its adhesion to the pestle no tablet showed exudation of a liquid component and tableting disorders such as adhesion of the tablet composition to the pestle. In addition, each of the tablets showed a hardness of 40 N or more, and had a practical tablet hardness (40 N or more) at which tablets are generally considered not to be abraded when they are conveyed in a process or transported in a state stored within a bottle.

Comparative Example 15

Tablets were produced using the same operation in Example 11 except for using cellulose powder H prepared in Comparative Example 3 in place of cellulose powder A from Example 11. The physical properties of the tablets are shown in Table 3. The tablets had the tableting disorder such as lamination that generated insufficient hardness probably because they could not retain a liquid component exuded under high tableting pressure.

Example 12

In a polyethylene bag for 3 minutes, 200 g of commercial ibuprofen pulverized with a small-size pulverizer (screen diameter φ: 1.5 mm, 1,4000 rpm), 265 g of a commercial granulated lactose "Super-Tab" (from Lactose New Zealand Ltd.) 25 g of cellulose powder E of the invention, and 10 g of croscarmellose sodium (Nichirin Chemical Industries, Ltd.) were mixed, to which 2.5 g of magnesium stearate (Taihei Chemical Industrial Co., Ltd.) was then added, followed by further slowly mixing for 30 seconds to make a mixed powder. The mixed powder was subjected to tableting at a turn table rotation rate of 54 rpm and a compressive force of 6,000 N using a 0.8-cm-diameter R pestle (12R) having an impression on the top surface in a rotary tableting machine (Cleanpress Correct 12HUK, Open Feeder, from Kikusui Seisakusho Ltd.). The results are shown in Table 4. The sticking rate (the percentage obtained by dividing the number of tablets that stick by the total number of tablets was observed usually and was 0% after tableting for 30 minutes.

Comparative Example 16

When 25 g of light anhydrous silicic acid (from Nippon Aerosil Co., Ltd.) was used in place of cellulose powder E of the invention, tableting was carried out using a similar operation to that in Example 12. The results are shown in Table 4. As for the tablet obtained by tableting for 30 minutes, the sticking occurred, and other tableting disorders such as the generation of crack on the tablet surface were also induced, and the hardness did not satisfy a practical hardness (40 N or more). In addition, as the result of testing 20 tablets under conditions of 25 rpm and 4 minutes using a friability tester (Pharma Test, from Japan Machinery Co.), the tablets had high weight reduction rates (friability) and were not desirable tablets.

TABLE 1

|  |  | Cellulose Powder | Polymerization Degree (–) | Average Size of Particles in A Dispersion Liquid (μm) | Average Particle Size (μm) | Apparent Specific Volume (cm³/g) | PEG400 Retention (%) |
|---|---|---|---|---|---|---|---|
| Examples | 1 | A | 310 | 67 | 50 | 9.5 | 290 |
|  | 2 | B | 270 | 54 | 230 | 7.5 | 326 |
|  | 3 | C | 160 | 59 | 60 | 8.2 | 434 |
|  | 4 | D | 440 | 51 | 47 | 7.6 | 190 |
|  | 5 | E | 300 | 65 | 45 | 12.5 | 400 |
| Comparative Examples | 1 | F | 440 | 41 | 38 | 6.3 | 183 |
|  | 2 | G | 220 | 29 | 49 | 3.1 | 135 |
|  | 3 | H | 488 | 50 | 50 | 7.3 | 239 |
|  | 4 | I | 1030 | No Dispersion | 105 | 12.5 | 250 |
|  | 5 | J | 220 | 29 | 4 | 8.3 | 155 |
|  | 6 | K | 440 | 41 | 60 | 7.2 | 186 |
|  | 7 | L | 220 | 29 | 100 | 8.9 | 187 |

* No use of cellulose dispersion

TABLE 2

|  |  | Cellulose Powder | Tablet Hardness (N) |
|---|---|---|---|
| Examples | 6 | A | 52 |
|  | 7 | B | 62 |
|  | 8 | C | 85 |
|  | 9 | D | 40 |
|  | 10 | E | 82 |
| Comparative Examples | 8 | F | 35 |
|  | 9 | G | 32 |
|  | 10 | H | 34 |
|  | 11 | I | 25 |
|  | 12 | J | 30 |
|  | 13 | K | 37 |
|  | 14 | L | 37 |

TABLE 3

|  |  | Cellulose Powder | Tableting Pressure (N) | Physical Properties of Tablet | |
|---|---|---|---|---|---|
|  |  |  |  | Hardness (N) | Incidence of Tableting Disorder (%) |
| Examples | 11 | A | 5000 | 61 | 0 |
|  |  |  | 10000 | 61 | 0 |
|  |  |  | 15000 | 59 | 0 |

TABLE 3-continued

| | Cellulose Powder | | Tableting Pressure (N) | Hardness (N) | Physical Properties of Tablet Incidence of Tableting Disorder (%) |
|---|---|---|---|---|---|
| Comparative Examples | 15 | H | 5000 | 32 | 0 |
| | | | 10000 | 36 | 24 |
| | | | 15000 | 34 | 13 |

TABLE 4

| | Tablet Hardness (N) | Tablet Friability (%) | Sticking Rate (%) |
|---|---|---|---|
| Examples | 12 | 75 | 0.05 | 0 |
| Comparative Example | 16 | 45 | 1.5 | 3 |

INDUSTRIAL APPLICABILITY

The present invention relates to a cellulose powder, a method for preparing the cellulose powder, and a molded article composition containing the cellulose powder and one or more active ingredients. The composition is useful as an excipient for a molded article containing an active ingredient, which is used in the field of medicine, food, or other chemical industries, and particularly as an excipient for medical tablets.

The invention claimed is:

1. A cellulose powder, having;
an average polymerization degree of 150 to 450; an average particle size of 30 to 250 μm; an apparent specific volume of more than 7 cm³/g; and
a retention capacity for polyethylene glycol with a molecular weight of 400 of 190% or more as calculated by the following formula:

(weight of polyethylene glycol 400 absorbed)×100/
(weight of the cellulose powder).

2. A method for preparing cellulose powder according to claim 1, comprising:
drying a cellulose dispersion liquid containing cellulose dispersion particles composed of a natural cellulosic material hydrolyzed to have an average polymerization degree of 150 to 450 and a medium, wherein the cellulose dispersion particles have an average particle size of 50 μm or more.

3. A molded article composition, comprising:
one or more active ingredients and the cellulose powder according to claim 1.

4. A method for preparing cellulose powder, comprising:
hydrolyzing natural cellulosic material at a temperature of from 40° C. to less than 60° C. and producing a cellulose dispersion liquid containing cellulose dispersion particles; and
drying the cellulose dispersion liquid to produce a cellulose powder have an average polymerization degree of 150 to 450, the cellulose powder having particles with an average particle size of 50 μm or more.

5. A method for preparing cellulose powder according to claim 4, wherein the cellulose powder has an apparent specific volume of more than 7 cm³/g.

6. A method for preparing cellulose powder according to claim 4, wherein the cellulose powder has a retention capacity for polyethylene glycol with a molecular weight of 400 of 190% or more as calculated by the following formula:

(weight of polyethylene glycol 400 absorbed)×100/
(weight of the cellulose powder).

* * * * *